United States Patent

Lown et al.

[11] 4,223,683
[45] Sep. 23, 1980

[54] HEART BEAT CUMULATOR

[75] Inventors: Bernard Lown, 194 Hobart Rd., Newton, Mass. 02159; Nicholas Jordan, Boston, Mass.

[73] Assignee: Bernard Lown, Newton, Mass.

[21] Appl. No.: 955,792

[22] Filed: Oct. 30, 1978

[51] Int. Cl.³ .............................................. A61B 5/04
[52] U.S. Cl. .................................................. 128/706
[58] Field of Search .............................. 128/706–711; 364/415–417

[56] References Cited

U.S. PATENT DOCUMENTS

| 3,590,811 | 7/1971 | Harris | 128/708 |
| 3,820,025 | 6/1974 | Lahr et al. | 128/706 |
| 3,853,119 | 12/1974 | Peterson et al. | 128/708 |
| 3,995,624 | 12/1976 | Maas | 128/708 |
| 4,034,745 | 7/1977 | Bloom | 128/706 |
| 4,073,011 | 2/1978 | Cherry et al. | 128/706 |

FOREIGN PATENT DOCUMENTS 540625 12/1976 U.S.S.R. .................................. 128/708

Primary Examiner—Robert W. Michell
Assistant Examiner—Francis J. Jaworski
Attorney, Agent, or Firm—Wolf, Greenfield & Sacks

[57] ABSTRACT

A heart beat cumulator records the number of heart beats occurring in each of a succession of ten minute intervals. An electrical signal of heart activity obtained from electrodes on the subject is amplified and applied to the input of a filter having a pass band of about 15Hz to 25Hz. The output of the filter is fed to a peak follower that provides a reference signal to a comparator which is actuated when the amplitude of the output of the filter exceeds the amplitude of the reference signal. Upon actuation of the comparator, the comparator emits a heart beat signal and triggers a monostable multivibrator that blocks the input to the comparator for about one third of a second. The heart beat signal is fed to a data counter. After each ten minute interval, measured by an internal electronic clock, the count in the data counter is written into a memory and the memory is then advanced by an address counter to a new address to condition the memory to record the count for the next ten minute interval at the new address.

3 Claims, 3 Drawing Figures

HEART BEAT CUMULATOR

FIELD OF THE INVENTION

This invention relates in general to apparatus for detecting and recording the beats of a heart. More particularly, the invention pertains to a portable device that detects and records the number of heart beats occurring in each of a succession of time intervals over a prolonged period of time.

BACKGROUND OF THE INVENTION

It is well known that the rate at which the heart beats is variable to enable the heart's delivery of blood to adapt to the needs of the body. Regulation of heart rate is achieved by nervous activity mediated by neural stimuli and circulating neurochemical agents. Each individual has an intrinsic heart rate level which is a function of heredity, age, sex, nervous temperament, body weight, physical condition, and health of the cardiovascular system. The heart rates occurring in periods of rest and in periods of activity varies about the intrinsic heart rate level of the individual.

It has been customary for the physician, since the beginning of recorded history, to give attention to the arterial pulse reflecting the heart beat. In general, it is customary to count the beats of the heart over a fraction of a minute and to then express the count as a minute rate. Cardiac tachometers are now available which quickly measure that minute rate.

There is a need for a device that permits correlation of heart rate with diurnal bodily rhythms, with diverse activities, and with psychological stresses. A record of heart rates occurring over a prolonged period of time such as twenty four hours or more can provide significant information regarding the state of cardiovascular health, the state of nervous tension, the action of drugs, as well as the effect of various stresses on the cardiovascular system.

OBJECT OF THE INVENTION

The objective of the invention is to provide a small, portable device for counting heart beats during successive time intervals over a prolonged period of time and recording the number of beats occurring in each interval.

In the embodiment of the portable heart rate cumulator here described a time interval of ten minutes has been selected and the device is capable of recording heart beats in successive intervals over a period of nearly two days.

SUMMARY OF THE INVENTION

In the preferred embodiment of the invention, an electrical signal related to heart activity is obtained from two electrodes disposed on the subject in the manner employed in electrocardiography. For ease of exposition, that signal is here termed the "electrocardio signal." The electrocardio signal is amplified and the amplified signal is fed into a bandpass filter having its pass band extending from about 15 Hz to 25 Hz. The filter's output is fed to a peak follower that provides a reference signal to a comparator against which the peak amplitude of the filtered QRS signal is measured. The peak follower prevents any signal whose amplitude is below the reference signal from affecting the comparator. The filtered QRS signal causes the comparator to be actuated and emit a "heart beat" signal that is fed to a heart beat counter. To prevent spurious actuation of the comparator, the comparator's input is blocked for about one third of a second upon the emission from the comparator of a "heart beat" signal. Blockage of the comparator is caused by a monostable multivibrator triggered by the "heart beat" signal output of the comparator. The "heart beat" signal from the comparator is fed to a data counter whose count is transferred into a memory. After each ten minute interval, measured by an internal electronic clock, the last count in the counter is stored in the memory and the memory is advanced by an address counter to a new address to enable recording of the count for the next ten minutes. The memory, thus, records the heart heat count for successive ten minute intervals. If desired, intervals of less than ten minutes may be chosen. However, shorter intervals require more memory capacity as more entries must then be recorded. As a corollary, less memory capacity is needed, if intervals of longer than ten minutes are chosen.

THE DRAWINGS

DETAILED DESCRIPTION OF THE PREFERRED EMBODIMENT

Figure 1:
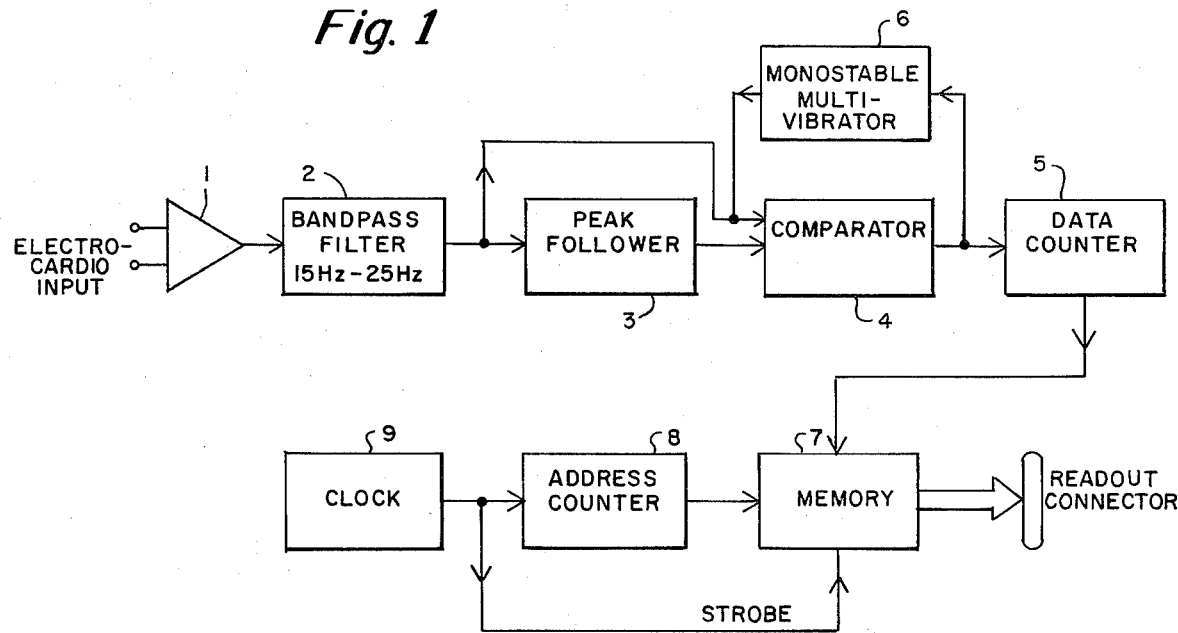
FIG. 1 is a block diagram showing the scheme of the preferred embodiment of the invention.

The scheme of the invention is diagrammatically shown in FIG. 1 where a preamplifier 1 is arranged to amplify the electrocardio input signal obtained from two electrodes situated on the chest wall of the subject in a bipolar position so as to generate the maximum QRS amplitude.

Figure 3:
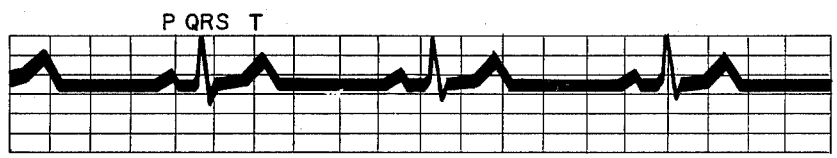
FIG. 3 is an electrocardiogram of a normal heart.

An electrocardiogram of a normal heart is depicted in FIG. 3. In that electrocardiogram, a low amplitude pulse, termed the "P wave", is caused by atrial excitation and is followed by a "PR segment" resting interval denoting passage of electrical impulses from atria to ventricles. The high amplitude deflection and fall following the PR segment is termed the "QRS group" and denotes ventricular excitation. Ventricular recovery is denoted by the "T wave" which, although of high amplitude, is below the peak amplitude of the QRS signal. A low deflection "V wave", not shown, occasionally follows the T wave.

The output of preamplifier 1 is fed to a bandpass filter 2 whose center frequency is about 20 Hz. The filter is arranged to pass signals in the band from about 15 Hz to 25 Hz. The output of the bandpass filter is applied to a peak follower 3 which is arranged to follow the peak amplitude of the signals emanating from the bandpass filter. The peak follower provides a reference signal to comparator 4 against which the peak amplitude of the filtered QRS signal is measured. Where the compared signal is above the amplitude of the reference signal, the comparator emits an output signal to a data counter 5 which counts the heart beats. To prevent high amplitude T signals from actuating the comparator, the output signal of the comparator is arranged to trigger a monostable multivibrator 6. The multivibrator, upon being triggered, emits a signal that blocks the comparator's input for a sufficient period to insure that other high amplitude signals which follow the QRS peak do not cause a false count. The duration of the blocking signal is long enough to insure that the next high amplitude signal following the end of the blocking period is the QRS signal.

Data counter 5 is arranged to transfer its count to a memory 7 which records the transferred count at an address determined by a memory address counter 8. An electronic clock 9 is arranged to emit a signal at ten minute intervals to the address counter 8 and the memory 7. The clock signal causes the count of the data counter 5 to be recorded in the memory. The clock signal is also applied to address counter 8 and causes that counter to advance its count. The address counter then causes the next entry into the memory to be recorded at a new address. At each successive ten minute interval therefore, the memory address counter is advanced and causes the memory to record the count of data counter 5 at a new address.

Figure 2:
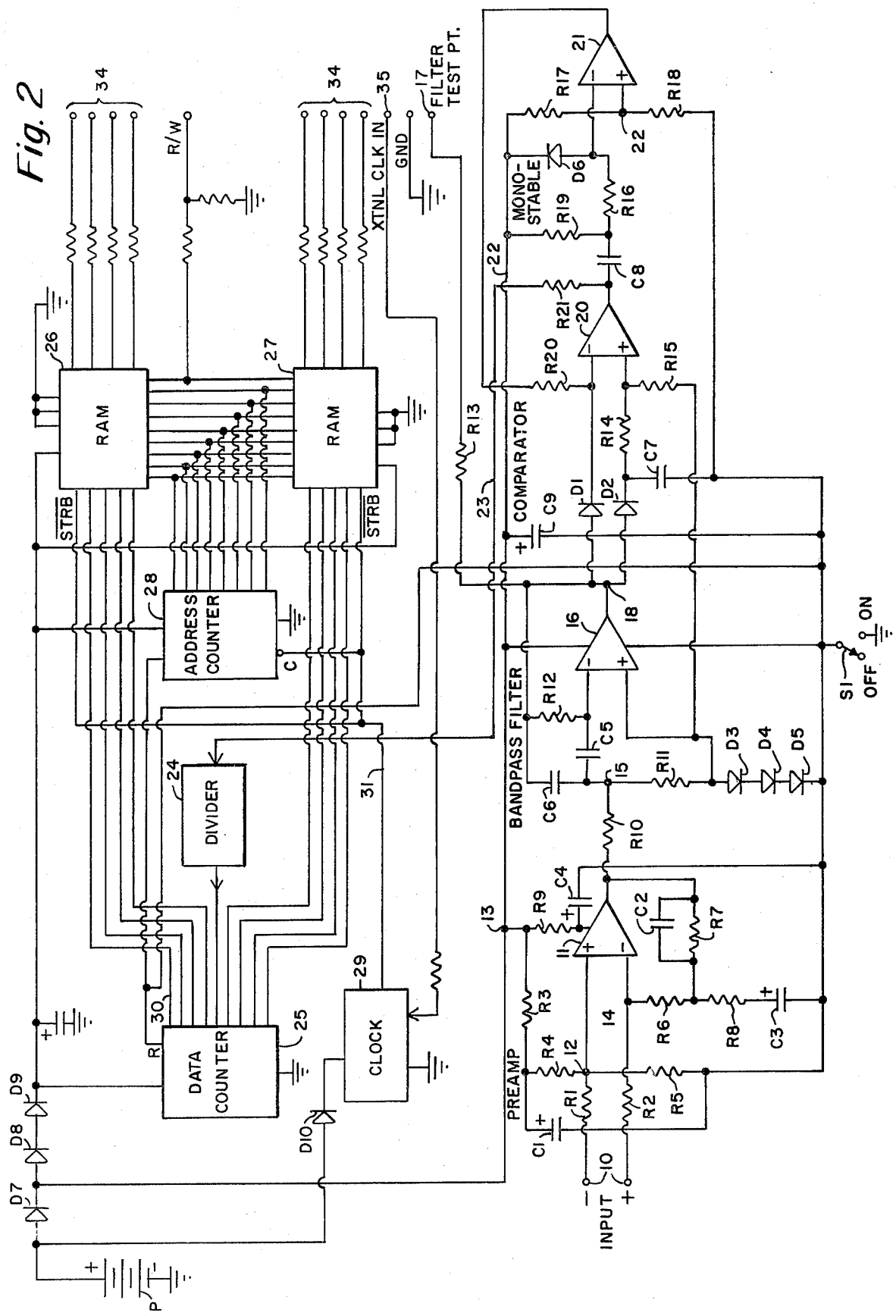
FIG. 2 is a circuit diagram of the preferred embodiment of the invention.

FIG. 2 is a circuit diagram of the preferred embodiment of the invention. In that embodiment an integrated circuit chip having four operational amplifiers is employed. The electrocardio signal picked up by the electrodes on the subject is applied at the input terminals 10 of the preamplifier which utilizes the operational amplifier 11.

The heart rate cumulator embodiment depicted in FIG. 2 is provided with a switch S1 which permits power from a power source to be applied to the electronic circuitry. Preferably, the power souce P is a battery so that the cumulator can be carried by the subject while a record of heart rates is made over an extended period of time. Because different power supply voltages are required for operation of the FIG. 2 embodiment, diodes D7, D8, and D9 are employed as voltage dropping devices to provide the requisite supply voltages.

Input terminals 10 are connected to the inverting and non-inverting inputs of operational amplifier 11 by resistors R1 and R2. The non-inverting terminal (+) is connected at junction 12 to a bias network consisting of resistors R3, R4, and R5 connected in series between voltage terminal 13 and ground. Fluctuations in the supply voltage are by-passed around resistors R4 and R5 by capacitor C1. The inverting input (−) is operational amplifier 11 is connected to a junction 14 and the output of operational amplifier 11 is fed back to that junction through a path having resistor R6 in series with a resistor R7 which is in parallel with a capacitor C2. The gain of amplifier 11 is determined by resistor R6, resistor R8, capacitor C3 all of which are connected in series between junction 14 and ground. The current drain of operational amplifier 11 is determined by the value of resistor R9. A capacitor C4 is provided to reduce the effects of supply voltage fluctuations on the current drain control. The output of the preamplifier is fed through a resistor R10 to the input junction 15 of the bandpass filter which is arranged to pass the band of frequencies from about 15 Hz to 25 Hz.

The bandpass filter is an active filter employing an operational amplifier 16 which has its inverting input coupled to input junction 15 by capacitor C5 and having its non-inverting input connected to that junction by resistor R11. The output of amplifier 16 is fed back to its inverting input through a resistor R12 and is fed back to junction 15 by a capacitor C6. For ease in checking the operation of the filter, its output is connected by a resistor R13 to a test point 17. The output of the bandpass filter at junction 18 is applied through a diode D1 to the inverting input of operational amplifier 20. The signal at junction 18 is also applied through a diode D2 to a storage capacitor C7 which provides a reference signal for the non-inverting input of operational amplifier 20 through resistor R14. The storage capacitor C7 is able to discharge through a path consisting of resistor R14, R15 and the diodes D3, D4, and D5. However, that capacitor cannot fully discharge through that path because the diodes D3, D4, and D5 become non-conductive when the forward bias drops below a minimum value. When the output signal from the bandpass filter has an amplitude exceeding the reference level set by capacitor C7, the comparator emits an output signal. That output signal from the bandpass filter also serves to recharge capacitor C7. In the interval between pulses from the output of the bandpass filter, capacitor C7 discharges through resistors R14 and R15 and diodes D3, D4, and D5. Diodes D3, D4, and D5 form a D.C. bias clipper because those diodes set a minimum level below which the signal is clipped.

To prevent the comparator from being affected by signals other than those derived from the QRS group, the output of the comparator is caused to trigger a monostable multivibrator which thereupon emits a pulse of 350 milliseconds duration. As shown in FIG. 2, the output of the comparator is coupled through capacitor C8 and resistor R16 to the inverting input of amplifier 21. The non-inverting terminal of that amplifier is connected at junction 22 to a bias network formed by resistors R17 and R18. Capacitor C8 is connected by resistor R19 to the positive voltage on line 22 and diode D6 is connected between that line and the inverting input of amplifier 21. The 350 millisecond output pulse of the multivibrator is fed through resistor R20 to the inverting input of operational amplifier 20. Consequently, the comparator is unable to revert to its original state until the 350 millisecond pulse ends and during that period the comparator is unaffected by signals passing through the bandpass filter.

The output of the comparator is fed via resistor R21 and line 23 to a binary counter 25. To avoid the necessity for employing a counter capable of counting to high numbers, the signal from the comparator is first fed to a divider 24 which emits a count signal for every eight signals from the comparator. The output of the divider is then fed to the input of an 8 bit binary counter 25 whose maximum count is 256. In actual practice the divider and binary counter are a single IC unit. Upon overflowing, that counter recommences to again count to 256 and continues to do so upon each overflow. During any ten minute interval, the counter may overflow once but will not overflow twice. The count in counter 25 is continually read out in parallel over lines 30 to a random access memory (RAM) comprised of two integrated circuit chips 26 and 27. The two chips are operated in parallel and essentially comprise a single memory. An address counter 28 controls the address in the RAMs where the count in counter 25 is recorded.

An electronic clock 29 is arranged to provide an output signal on line 31 at 10 minute intervals. The clock pulse strobes the RAMs and causes the output count of data counter 25 to be written into the RAMs. Thus upon the emission of a clock pulse the data count in counter 25 at the time of the occurrence of the strobe signal is entered in the memory. The clock pulse also actuates address counter 28 to cause the count to be advanced. The output of the address counter controls the address of both RAMs. Upon an advance in the count of the address counter, the RAMs are conditioned to record information at a new address.

The RAMs employed in the FIG. 2 embodiment have a maximum of 256 addresses and therefore can record the heart beats for 256 successive ten minute periods. The RAMs therefore can record the heart beats for a maximum period of 42 hours. If the heart beat cumulator is used for a period longer than 42 hours, the address counter causes new information to be written in the RAMs over the old information. Thus the heart beat cumulator records information only for the last 42 hours. Of course, where prolonged recording periods of greater than 42 hours are desired, RAMS having greater capacity can be employed. It is contemplated that in normal usage, a period of 42 hours is sufficient because the information in the RAMs would be read out and the instrument reset to begin recording anew.

To prevent information in the RAMs from being inadvertently destroyed by shutting off the instrument, it is preferably to employ RAMs of the non-volatile type so that recorded information is retained in the memory without requiring electrical power to be continuously applied to the RAMs.

Where RAMs of the volatile type are employed, the RAMs are arranged to have electrical power from the battery continuously available to enable the recorded information to be retained. To attain that objective, switch S1 is arranged to shut off power to the amplifiers without shutting off power to the RAMs. To prevent the volatile RAMs from draining the battery, it is preferred to use CMOS RAMs which have low power requirements for information retention.

The information stored in the RAMs can be read out at output terminals 34. To enable rapid read out, a source of external clock signals is applied at input 35 to cause the address counter 28 to be driven. At each address, the recorded information is read out at output terminals 34. After the recorded data is read out, the device can be placed in an initial state by resetting the data counter 25 and the address counter to zero.

In an embodiment of the invention constructed in accordance with the circuit diagram of FIG. 2, the four operational amplifiers 11, 16, 20, and 21 were on an XR4202 integrated circuit unit made by EXAR Corporation and the other components have the following values

| | |
|---|---|
| R1 = 1M | C1 = 1uf |
| R2 = 1M | C2 = 220pf |
| R3 = 4.7M | C3 = .47uf |
| R4 = 10M | C4 = .47uf |
| R5 = 10M | C5 = .01uf |
| R6 = 4.7M | C6 = .01uf |
| R7 = 10M | C7 = .22uf |
| R8 = 68K | C8 = .015uf |
| R9 = 10M | C9 = 1uf |
| R10 = 47K | |
| R11 = 2.2M | |
| R12 = 22K | |
| R14 = 4.7M | |
| R15 = 10M | |
| R16 = 100K | |
| R17 = 2.2M | |
| R18 = 10M | |
| R19 = 10M | |
| R20 = 10M | |

-continued

| |
|---|
| R21 = 100K | all diodes are Motorola MMD-70
Battery = 7 volt

It is obvious to those knowledgable in electronic circuitry that the invention can be embodied in forms quite different from that depicted in FIG. 2. Accordingly, the circuitry of FIG. 2 is exemplary only and it is intended that the invention not be limited to that embodiment but rather that the scope of the invention be delimited by the appended claims.

We claim:

1. In apparatus of the type having
   (1) means for obtaining an electrocardio input signal,
   (2) means for amplifying the electrocardio input signal,
   (3) a bandpass filter for filtering the amplified electrocardio signal,
   (4) means coupled to the output of the bandpass filter for deriving a reference signal related to the peak amplitude of the filtered electrocardio signals,
   (5) a comparator arranged to compare the filtered electrocardio signal with the reference signal, the comparator emitting a heart beat count signal when the amplitude of the filtered electrocardio signal exceeds the reference signal,
   (6) means for preventing actuation of the comparator for a period of time after emission of a heart beat count signal whereby activation of the counter by spurious signals is prevented, and
   (7) a heart beat signal counter coupled to the output of the comparator, the heart beat signal counter being arranged to count heart beat signals emitted by the comparator, the improvement of apparatus for separately recording for each interval the number of heart beats occurring in each of a succession of intervals, the improvement comprising
   (a) a memory device having a plurality of recording addresses, the heart beat signal counter being coupled to the memory device for transmission of its count thereto,
   (b) a clock arranged to periodically emit clock signals, and
   (c) an address counter for controlling the address at which information from the heart beat signal counter is recorded in the memory device, the address counter responding to clock signals by causing information from the heart beat signal counter to be recorded at a new address at periodic intervals.

2. The improvement according to claim 1, wherein
   (i) the heart beat signal counter is of the type that returns to a datum count upon overflow of the counter, and
   (ii) the duration of each interval is such that the counter will not overflow twice in the same interval.

3. The improvement according to claim 1, wherein
   (i) each interval is of at least several minutes duration, and
   (ii) the address counter is arranged to count the clock signals and cause the recordation of information in the memory device at new addresses as the count increases.

* * * * *